(12) United States Patent
Dodt

(10) Patent No.: US 9,759,661 B2
(45) Date of Patent: Sep. 12, 2017

(54) DEVICE FOR THE OPTICAL IMAGING OF A SAMPLE

(75) Inventor: Hans-Ulrich Dodt, Munich (DE)

(73) Assignee: Hans-Ulrich Dodt, Munich (DE)

( * ) Notice: Subject to any disclaimer, the term of this patent is extended or adjusted under 35 U.S.C. 154(b) by 380 days.

(21) Appl. No.: 13/055,755

(22) PCT Filed: Feb. 12, 2009

(86) PCT No.: PCT/EP2009/000997
§ 371 (c)(1),
(2), (4) Date: Feb. 17, 2011

(87) PCT Pub. No.: WO2009/100911
PCT Pub. Date: Aug. 20, 2009

(65) Prior Publication Data
US 2011/0186754 A1 Aug. 4, 2011

(30) Foreign Application Priority Data
Feb. 12, 2008 (AT) .................... 228/2008

(51) Int. Cl.
*G01N 21/64* (2006.01)
*G02B 21/00* (2006.01)
(Continued)

(52) U.S. Cl.
CPC ..... *G01N 21/6458* (2013.01); *G01N 21/6486* (2013.01); *G02B 21/0076* (2013.01); *G01N 15/0205* (2013.01); *G02B 1/16* (2015.01)

(58) Field of Classification Search
None
See application file for complete search history.

(56) References Cited

U.S. PATENT DOCUMENTS 4,188,120 A * 2/1980 McDonald et al. .......... 356/318
6,548,796 B1 * 4/2003 Silvermintz et al. ...... 250/201.3
(Continued)

FOREIGN PATENT DOCUMENTS

DE 102006009833 A1 9/2007
WO WO 2006/114247 A1 11/2006

OTHER PUBLICATIONS

Klar et al. "Fluorescence Microscopy with Diffraction Resolution Barrier Broken by Stimulated Emission" PNAS 2000 vol. 97(15): 8206-8210.
(Continued)

*Primary Examiner* — Neil N Turk
(74) *Attorney, Agent, or Firm* — Licata & Tyrrell P.C.

(57) ABSTRACT

In a device for the optical imaging of a sample, having at least one light source for excitation light in order to excite a fluorescent dye in a sample, which is held by a sample holder, for spontaneous emission of fluorescent light over a limited period of time in a spatial region having increased resolution, and for de-excitation light in order to de-excite the fluorescent dye again except for a residual zone that is reduced in size relative to the spatial region, wherein light from the sample having wavelengths other than those of the excitation light and of the de-excitation light is assignable to the spontaneous emission of fluorescent light from the residual zone of the spatial region (STED, GSD, etc.), the de-excitation light (3) is arranged to be transmitted in two parallel planes which are separated by a gap (2).

8 Claims, 2 Drawing Sheets

(51) Int. Cl.
   G01N 15/02     (2006.01)
   G02B 1/16      (2015.01)

(56)           References Cited

U.S. PATENT DOCUMENTS 7,646,481   B2    1/2010   Dyba et al. .................. 356/318
   2004/0212799 A1  10/2004   Hell ............................ 356/317
   2005/0035305 A1*  2/2005   Kleinfeld et al. ......... 250/458.1
   2007/0206278 A1*  9/2007   Dyba et al. .................. 359/385

OTHER PUBLICATIONS

Betzig et al. "Imaging Intracellular Fluorescent Proteins at Nanometer Resolution" Science 2006 313:1642-1645.

* cited by examiner

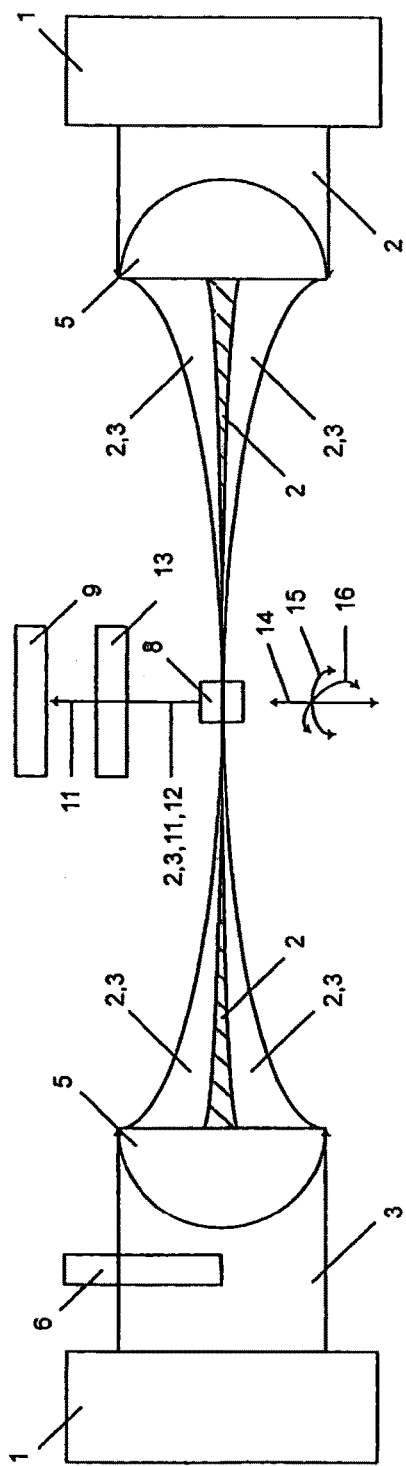
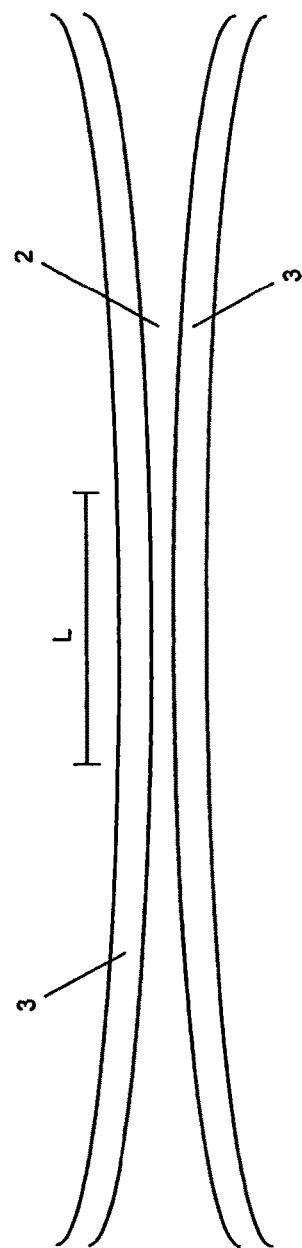
Fig. 2
Fig. 3

DEVICE FOR THE OPTICAL IMAGING OF A SAMPLE

The invention relates to a device for the optical imaging of a sample, having at least one light source for excitation light in order to excite a fluorescent dye in a sample, which is held by a sample holder, for spontaneous emission of fluorescent light over a limited period of time in a spatial region, and for de-excitation light in order to de-excite the fluorescent dye again except for a residual zone that is reduced in size relative to the spatial region, wherein light from the sample having wavelengths other than those of the excitation light and of the de-excitation light is assignable to the spontaneous emission of fluorescent light from the residual zone of the spatial region. The invention further relates to methods of improving the axial resolution using STED microscopy.

In the field of microscopy and especially in the field of ultra-microscopy, it has long been generally assumed that dimensions that lie below Abbé's diffraction limit cannot be imaged using optical methods. That assumption has been refuted, however, by new methods which are used, for example, in the 4-Pi microscope or the STED microscope.

WO 2006/114247 A1 shows and describes a fluorescence microscope based on the STED method or the more general RESOLFT method (acronym for reversible saturable optical fluorescence transitions) in accordance with Dr. Stefan Hell. In such a method, fluorescent particles are excited using an excitation light beam and are "quenched" again, i.e. their excitation is impeded, using a de-excitation light beam. In accordance with the laws of optics, neither light beam can be focussed more sharply than prescribed by Abbé's law. Since, however, the de-excitation light beam is zero at only a very small location, that location being at the centre of the point to be illuminated or observed, luminous dye also remains only at a very small location. In the case of STED, the de-excitation process employed is stimulated emission. The STED microscope is based in principle on the phenomenon of fluorescence. In the case of the more general RESOLFT method, in principle all optically saturable transitions involved in the fluorescence are suitable for transient shifting of a fluorescent molecule into a non-fluorescent state.

A fundamental problem of any optical microscopic technique is the lack of contrast between cell constituents, for which reason there have long been used fluorescent molecules which can be attached selectively to certain molecules of a cell, for example using genetic engineering methods or by means of antibodies. For example, dyes can be attached selectively to mitochondria. If a location in the cell so prepared is then illuminated using a focussed laser beam and fluorescence is received from that location, dye molecules and therefore also mitochondria were present at precisely that location. In order to obtain a complete image, the sample is scanned point by point.

The excitation light beam cannot be focussed as small as desired on account of Abbé's diffraction limit. Therefore all the molecules present in the focal spot at the time are always excited and so it is not possible to distinguish from which molecule the fluorescence is coming. Accordingly, structures smaller than the extent of the laser focus cannot be differentiated.

The mode of operation of STED microscopy is as follows: first of all, in exactly the same way as in conventional microscopy, a small area of a minimum of 200 nm (diameter) is excited by means of a focussed light beam. A second light beam of lower energy is transmitted a few picoseconds after the excitation beam, before the excited dye molecules are able to fluoresce spontaneously. Where that beam strikes an excited fluorescent marker, it de-excites that marker again. By applying the second beam in a ring around the previously excited location, a large proportion of the excited area (the edges) can be de-excited again before the spontaneous emission of fluorescence occurs. Accordingly, the emitting area—that is to say the centre of the ring—is effectively reduced in size. The detection of fluorescence then involves only those marker molecules which have not been de-excited. That can in theory be only a single molecule that was previously located in the centre of the excitation spot. The local resolution of the optical detector is immaterial.

In a STED microscope, it is possible to examine all specimens that can be labelled with fluorescent dyes. Unlike electron microscopes, a vacuum and thin sections are not required, because this is a far-field technique. The samples do not suffer radiation damage, so that living cells can also be observed.

The problem of the invention is now to improve the described device to the effect that the scan times are reduced and that the time required to create a 3D image is reduced overall.

To solve that problem, according to the invention it is proposed to develop the device of the kind mentioned at the beginning in such a way that the excitation light and the de-excitation light are arranged to be transmitted in two parallel planes, the excitation plane lying between the two de-excitation planes which are separated by a complete or approximate zero intensity point (distinct minimum). As a result, it is possible not only to scan merely individual points sequentially but also to scan whole planes at once, which results in a reduction in the time required for scanning a sample. The detection device, i.e. its optical axis, is located substantially perpendicular to the excitation plane, so that in the case of imaging the sample onto a planar detector the total excitation plane that has been rendered thin by de-excitation is detected. De-excitation light is here to be understood as being any kind of radiation which does not allow the particles illuminated by that light to fluoresce, although those particles are also illuminated by excitation light.

In a preferred development of the device according to the invention, the excitation light and/or the de-excitation light is focussed into one plane by at least one cylindrical lens. By the use of a cylindrical lens it is possible to focus the excitation and de-excitation light into one plane. The focussing of excitation light and de-excitation light can be effected by the same cylindrical lens or by two cylindrical lenses located opposite one another.

In a preferred development of the device, the de-excitation light, by the intermediate arrangement of a half-wave plate, is excited for destructive interference in the sense of extinction in one plane. As a result, the thickness of the plane in which no de-excitation light is transmitted is kept to a minimum. By virtue of the formation of that hollow light plane by means of a half-wave plate, the plane in which the fluorescence emission takes place can be made up to 10 times thinner in comparison with the methods from the prior art or even thinner. This is because the hollow light plane has a central zero intensity point. By increasing the intensity of the de-excitation radiation of that plane it is possible for the fluorescence plane still emitting to have almost any desired thinness, resulting in an improvement in axial resolution.

In an advantageous development of the device, the excitation light is automatically directed substantially into the gap between the two parallel planes of the de-excitation light. This is achieved by the excitation and de-excitation beam paths' overlapping and being centred in such a way that the hollow de-excitation beam path encloses the excitation beam path. It requires only one cylindrical lens to form the light plane of the excitation light beam, and the transmission plane is determined by the alignment of the cylindrical lens. The point alignment of a common centre of the excitation and de-excitation light is simple to achieve with a laser and the planes can be defined by rotation of the cylindrical lens or of the cylindrical lens in combination with the half-wave plate. This has the result, in a simple way, that the excitation light is introduced substantially only in the gap between the two de-excitation light planes.

In a variant of the device, the de-excitation light and the excitation light are introduced from different directions. Although, in that case, it is necessary to align the beam paths, when two different sources are used they can be arranged so that they do not obstruct one another.

In a further variant of the device, the sample holder is movable translationally in a direction substantially perpendicular to the illumination plane of the excitation and de-excitation light. As a result, the sample can in a simple way be scanned in individual planes, which keeps down the time required for a complete scan.

In a further variant of the device, the sample holder is pivotable about at least one axis, preferably two axes. As a result, in combination with the translational movability of the sample holder, a complete scan of a sample in three dimensions can be achieved in a simple way: after a first scan, the sample is twice turned through 90 degrees about two mutually perpendicular axes and subsequently the sample is moved translationally through the illumination plane. The pivotability about two axes thus makes it simple to define three orthogonal image planes in x, y and z, which are then scanned translationally plane by plane.

In a development of the device, a computer is provided for recording and correlating the optical data. The recordings in one scan direction are stored in stacks and can subsequently be processed by the computer to form a 3D image, for which, of course, depending upon the data or the size of the sample, considerable computing resources are required. Such processing in 3D, however, subsequently enables the resolution in each individual plane to be increased. Simulating the sample on the computer provides the observer with a simple way of viewing the sample also from directions in which no data at all has been recorded, it also being possible for more than three stacks of image planes to be combined with one another by the computer.

The invention relates also to a method of using the device according to the invention and to a method of improving axial resolution in the imaging of a sample using a device in accordance with any one of the preceding claims, the recorded data being correlated by a computer and assembled to form a 3D image. In that procedure, when the three data stacks recorded with displacement in x, y and z are superimposed, the lower resolution in each case is compensated in the axial direction.

The method can be carried out in such a way that further methods of increasing the lateral resolution, such as, for example, PALM, are combined and/or used. In the case of the PALM method (Betzig E, Science 313: 1642-1645 (2006) (also known as PALMIRA or STORM), ten times higher resolution is obtained in x and y, which can be combined with the improved z resolution achieved herein, the fluorescent particles being irradiated with a short, intensive pulse of excitation light, but each time only a small number of fluorescent particles, which, in addition, are widely spaced, begin to emit light. Once those particles have ceased to emit light, a further pulse of excitation light can be transmitted. Because the transition from non-fluorescence to fluorescence is stochastic, however, different fluorescent particles are activated each time and on each imaging operation the position of the luminous particles can be very well approximated by back-calculation of the point spread function, for example by superimposition of the image points with a Gaussian curve. Since those image points are each recorded separately, the resolution can be increased in comparison with an image that is limited in its resolution by diffraction.

That method can be used in a large number of fields, the method being used especially in pathology but also being usable in checking or representing semiconductor topologies.

The invention is described in greater detail below with reference to exemplary embodiments shown in diagrammatic form in the drawings, wherein

BRIEF DESCRIPTION OF THE FIGURES

FIG. 2 shows a further spatial layout for the planes of the excitation and de-excitation light and FIG. 3 shows on an enlarged scale the central region in which the planes intersect.

DETAILED DESCRIPTION OF EMBODIMENT

Figure 1:
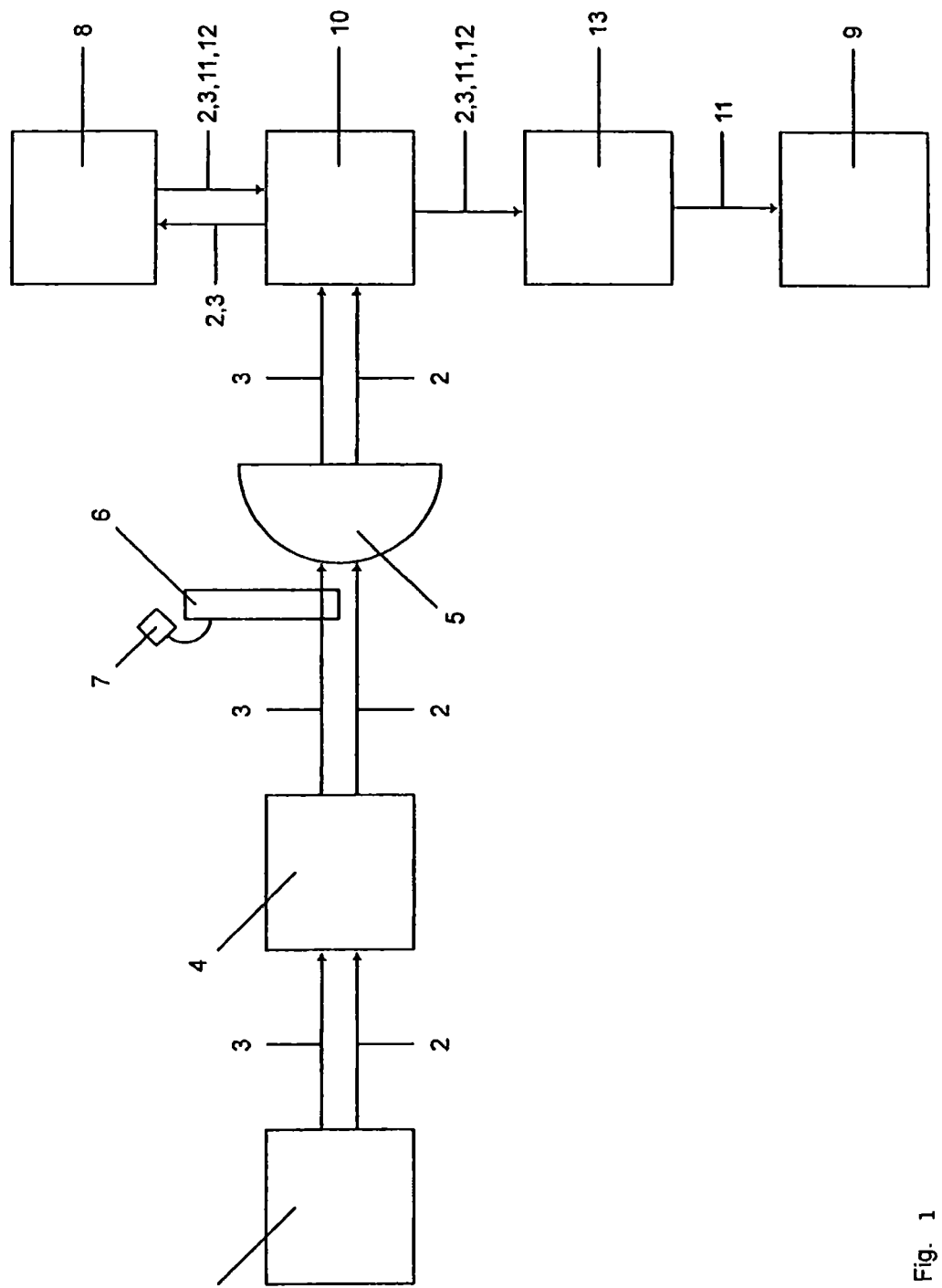
FIG. 1 is a block diagram of the layout of the fluorescence microscope.

In FIG. 1, reference numeral 1 indicates a mode-coupled laser which in this form serves as a pulsed or CW light source for the excitation light 2 and de-excitation light 3. The latter are emitted simultaneously and in the case of mode-coupled lasers are together guided into a delay generator 4 in which a time delay between the pulses of the excitation light 2 and the pulses of the de-excitation light 3 is produced. Both the de-excitation light 3 and the excitation light 2 are subsequently guided through a cylindrical lens 5 in order to form respective light planes; in the case of the de-excitation light 3, a half-wave plate 6, for example, is arranged between the delay generator 4 and the cylindrical lens 5 in order to form a hollow light plane. For that purpose it is also possible, however, to use other suitable optical means, such as digital-optical means, holographic means or means that serve to generate a hollow Bessel beam.

If the de-excitation light 3 and the excitation light 2 are both focussed by the same cylindrical lens 5, an actuating means 7 can be provided which moves the half-wave plate 6 out of the light beam when the excitation light 2 passes through the cylindrical lens 5. The excitation and de-excitation radiation can also be superimposed by means of a dichroic mirror. The hollow light plane of the de-excitation light 3 and the light plane of the excitation light 2 is subsequently directed onto the sample 8, the coupling-in device being indicated diagrammatically by reference numeral 10. Both the excitation light 2 and the de-excitation light 3 are directed onto the sample 8 by the coupling-in device. Then in addition to the scattered portions of the excitation light 2 and of the de-excitation light 3, the fluorescent light 11 of the sample 8 is also transmitted from the sample 8. That light spectrum is subsequently filtered through a filter device 13, so that only the fluorescent light 11 reaches the photodetector 9.

FIG. 2 shows a different spatial layout in which the de-excitation light 3 is directed onto the sample 8 from the opposite side to the excitation light 2, the sample 8 being movable perpendicular to the illumination plane in the direction of the double-headed arrow 14. The sample 8 is subsequently pivotable in the direction of the two double-headed arrows 15 and 16.

FIG. 3 shows the geometry of the illumination plane; the greatest diameter of the sample should be smaller than the length L in which the two de-excitation light planes are approximately parallel.

The invention claimed is:

1. A device for the optical imaging of a sample comprising at least one light source arranged for transmitting excitation light in a plane in order to excite a fluorescent dye in a sample, which is held by a sample holder, for spontaneous emission of fluorescent light over a limited period of time in a spatial region and generating a total excitation plane through the sample, and for de-excitation light in order to de-excite the fluorescent dye again except for a residual zone that is reduced in size relative to the spatial region, wherein light from the sample comprising wavelengths other than those of the excitation light and of the de-excitation light is assignable to the spontaneous emission of fluorescent light from the residual zone of the spatial region, wherein the de-excitation light is arranged to be transmitted in two parallel planes which are separated by a gap for the excitation plane, and an imaging planar detector located substantially perpendicular to the excitation plane and configured to image the excitation plane by detecting fluorescent light from the total excitation plane through the sample.

2. The device of claim 1, wherein at least one cylindrical lens focuses the excitation light and/or the de-excitation light into one plane.

3. The device of claim 2, further comprising a half-wave plate arranged relative to the cylindrical lens to form a hollow light plane.

4. The device of claim 1, wherein the de-excitation light and the excitation light are transmitted from different directions.

5. The device of claim 1, wherein the sample holder is movable translationally in a direction substantially perpendicular to the illumination plane of the excitation and de-excitation light.

6. The device of claim 1, wherein the sample holder is pivotable about one or more axes.

7. The device of claim 1, further comprising a computer for recording and correlating optical data.

8. The device of claim 7, further comprising PALM to increase lateral resolution.

\* \* \* \* \*